United States Patent [19]

Borer et al.

[11] Patent Number: 4,639,135
[45] Date of Patent: Jan. 27, 1987

[54] CUVETTE

[75] Inventors: Claude Borer, Hünenberg; Andreas Greter, Steinhausen, both of Switzerland

[73] Assignee: Hoffmann-La Roche Inc., Nutley, N.J.

[21] Appl. No.: 702,522

[22] Filed: Feb. 19, 1985

[30] Foreign Application Priority Data

Feb. 23, 1984 [CH] Switzerland .......................... 896/84

[51] Int. Cl.$^4$ .......................................... G01N 21/03
[52] U.S. Cl. ................................................. 356/246
[58] Field of Search ........................................ 356/246

[56] References Cited

U.S. PATENT DOCUMENTS 3,441,383  4/1969  Moore et al. .
3,811,780  5/1974  Liston ........................... 356/246
4,126,418  11/1978  Krasnow ...................... 356/246 X

FOREIGN PATENT DOCUMENTS 100663  2/1984  European Pat. Off. .
2470963  6/1981  France .......................... 356/246

OTHER PUBLICATIONS

Hitachi Analyzer Model 705, eight photographic prints and 13 photocopied pages of trade literature (as supplied by applicants).

Primary Examiner—Vincent P. McGraw
Attorney, Agent, or Firm—Jon S. Saxe; Bernard S. Leon; Richard J. Mazza

[57] ABSTRACT

A cuvette arrangement for use in a chemical analysis system, which cuvette arrangement comprises an integrally constructed unit which defines separate chambers, for the receipt of sample-reagent mixtures.

In order to overcome difficulties which arise in the use of the cuvette arrangement, and to reduce the manufacturing costs thereof, it is formed as a cuvette ring segment which possesses means for positioning it in the analysis system, each chamber possessing the following elements: an open and a closed end, an outer side wall forming an outer edge which fits into a first arc, an inner side wall forming an inner edge which fits into a second arc concentric with the first arc, a bottom wall extending between the outer and inner side walls at the closed end of the chamber, and windows which enable radiation energy to be transmitted through the chamber with low loss and free from distortion, which windows comprise a pair of flat, mutually parallel parts which are separated from one another by a defined distance, one of the flat parts in each pair being integrated with the outer side wall and the other of the flat parts in each pair being integrated with the outer side wall and the other of the flat parts in each pair being integrated with the inner side wall.

2 Claims, 4 Drawing Figures

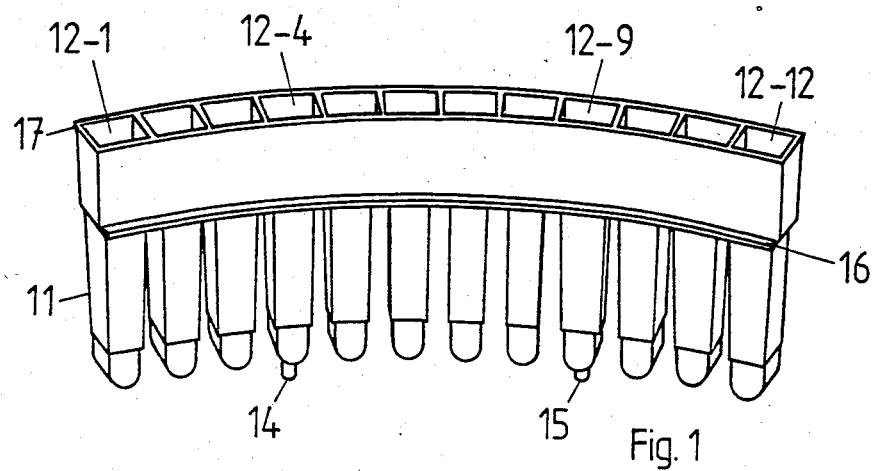
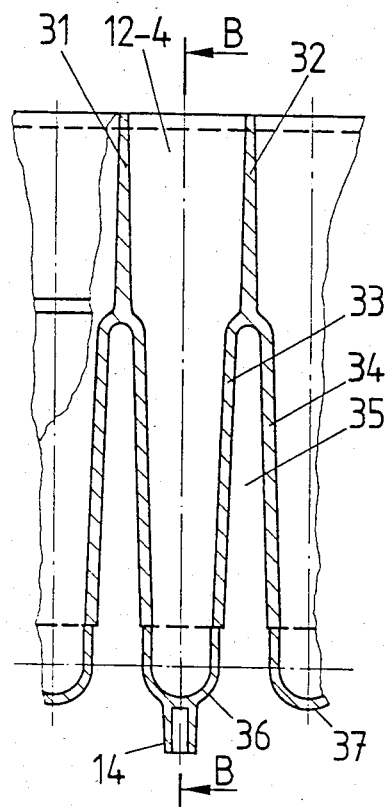
Fig. 3
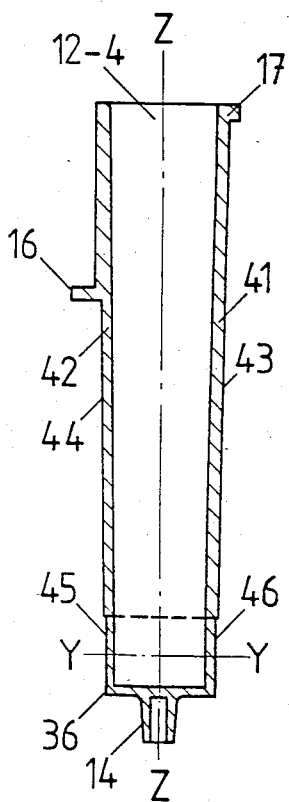
Fig. 4

CUVETTE

BACKGROUND OF THE INVENTION

The invention relates to a cuvette arrangement for use in a chemical analysis system, which cuvette arrangement comprises an integrally constructed unit which defines a plurality of separate chambers, for receiving a plurality of sample-reagent mixtures.

Cuvette arrangements of this type are known in the form of disposable cuvette rings which, for example, comprise 100 cuvettes. Completely annular cuvette rings of this type have the following disadvantages:

The user is frequently unable to use all the cuvettes of the cuvette ring within one working cycle. Nevertheless, the whole cuvette ring must often be thrown away, because it contains liquids or liquid residues, which must be removed from the analysis system as rapidly as possible or, at the latest, at the end of the working day. This reduces the rate of utilization of the cuvette rings.

Cuvette rings, in particular those which contain a relatively large number of cuvettes and have therefore a relatively large diameter, tend to suffer distortion. The resulting deformations of the cuvette ring impair the performance of optical measurements of the cuvette contents in an analysis system, because very exact positioning of all the cuvettes of the cuvette ring is necessary for such measurements. In order to minimize the extent of such deformations, a relatively complex shaping of the cuvette rings and special packaging of the latter are necessary. This increases the manufacturing costs for the cuvette rings and their selling price. Moreover, when the cuvette rings are used in an analysis system, means must be provided in the latter which enable all the cuvettes to be positioned accurately, even if the cuvette rings are slightly distorted. This increases the manufacturing costs of the analysis system.

It is therefore the object of the invention to provide a cuvette arrangement which does not suffer from the abovementioned disadvantages.

SUMMARY OF THE INVENTION

According to the invention, this object is achieved with a cuvette arrangement of the type hereinafter described in detail. This arrangement comprises an integrally formed, partially annular array of chambers; that is to say, it constitutes a cuvette ring segment. The cuvette arrangement further includes means for positioning it in an analysis system. Each chamber of the cuvette arrangement comprises the following elements: an open end and a closed end; an outer side wall forming an outer edge which fits into a first arc; an inner side wall forming an inner edge which fits into a second arc concentric with the first arc; a bottom wall extending between the outer and inner side walls at the closed end of the chamber; and windows which enable radiation energy to be transmitted through the chamber with low loss and free from distortion, which windows comprise a pair of flat, mutally parallel parts which are separated from one another by a defined distance, one of the flat parts in each pair being integrated with the outer side wall and the other of the flat parts in each pair being integrated with the inner side wall.

The cuvette arrangement according to the invention has made it possible to overcome all the above-mentioned disadvantages of the previously known cuvette rings and, furthermore, to obtain a reduction in the manufacturing costs of the cuvette arrangement.

A preferred embodiment of the cuvette arrangement according to the invention has a lip which is integrated with the inner side walls, extends radially from the latter on the outside of the chambers and can be used as means for positioning the cuvette arrangement in the analysis system. This embodiment has the advantage that it enables the cuvette arrangement to be positioned fairly accurately at very low cost.

In a particularly advantageous embodiment of the cuvette arrangement according to the invention, the bottom wall of at least one of the chambers has a projection which extends from the outside of the bottom wall along the longitudinal axis of the chamber and can be used as means for positioning the cuvette arrangement in the analysis system. In this case, the advantage is that an even more accurate positioning of the cuvette arrangement is possible at virtually negligible extra cost.

The cuvette arrangement according to the invention preferably contains a plurality of partitions integrated with the outer side walls, the inner side walls and the bottom walls of the chambers, each partition having an upper section, of which at least a part is located at the open end of a chamber, a first lower section integrated with the bottom wall of a first chamber, and a second lower section integrated with the bottom wall of a second chamber, the first and second lower sections being separated by an air space. With this structure, on the one hand, a relatively large number of chambers can be accommodated in one cuvette ring segment and, on the other hand, the temperature of the chamber contents can be controlled more easily and quickly.

An illustrative embodiment of the invention is explained in more detail below by reference to the attached drawings in which:

FIG. 1 shows a perspective view of a cuvette arrangement according to the invention.

FIG. 3 shows a cross-section along the line A—A in FIG. 2, and

FIG. 4 shows a cross-section along the line B—B in FIG. 3.

DETAILED DESCRIPTION OF THE INVENTION

Figure 2:
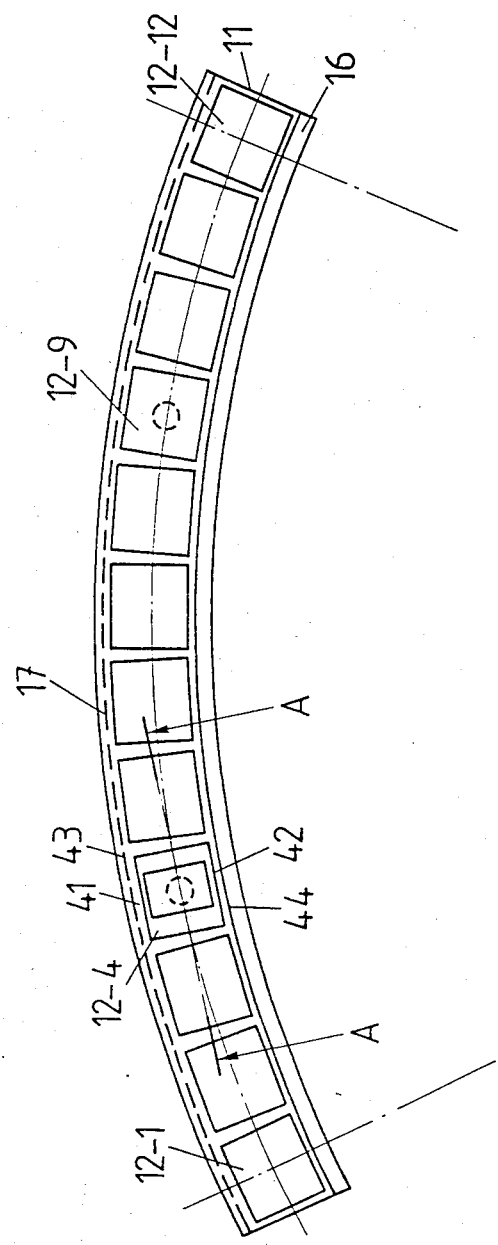
FIG. 2 shows a plan view of the cuvette arrangement in FIG. 1.

The cuvette arrangement according to the invention, shown in FIGS. 1 and 2, forms a partially annular cuvette ring segment 11. The latter is integrally formed, for example from glass-clear unstablized polymethyl methacrylate (PMMA). The cuvette ring segment 11 comprises 12 chambers, 12-1 to 12-12, in which 12 mutually separate samples can be mixed with suitable reagents and the sample-reagent mixture can be retained for optical analysis. As can be seen from FIGS. 1 and 2, these chambers are arranged along an arc. As shown by FIGS. 1-4, each of these chambers possesses the following elements: an open end and a closed end, an outer side wall 41 forming an outer edge 43 which fits into a first arc, an inner side wall 42 forming an inner edge 44 which fits into a second arc concentric with the first arc, a bottom wall 36 extending between the outer and inner side walls at the closed end of the chamber, and windows which enable radiation energy to be transmitted through the chamber with low loss and free from distortion, which windows comprise a pair of flat, mutually parallel parts 45, 46 which are separated from one another by a defined distance, one of the flat parts in each pair being intergrated with the outer side wall 41 and the other of the flat parts in each pair being integrated with the inner side wall 42.

All the chambers 12-1 to 12-12 have the same shape and the same dimensions. In order to indicate an order of magnitude of the dimensions of one of these chambers, such a chamber is, for example, 38 mm high and the distance between the outer edge 43 and the inner edge 44 amounts to, for example, 6 to 8 mm.

A complete cuvette ring can be formed with 6 cuvette ring segments like that shown in FIG. 1. Within the scope of the invention, however, the cuvette ring segment according to FIG. 1 can comprise more or less than 12 chambers. Depending on the selected number of chambers per segment, more or fewer such segments are then required to form a complete cuvette ring.

As shown in detail in FIG. 3, the cuvette arrangement according to FIG. 1 contains a plurality of partitions which are integrated with the outer side walls, the inner side walls and the bottom walls of the chambers, each partition having an upper section 31 or 32, of which at least a part is located at the open ends of a chamber, a first lower section 33 integrated with the bottom wall 36 of a first chamber, and a second lower section 34 integrated with the bottom wall 37 of a second chamber, the first and second lower sections being separated by an air space 35.

The cuvette ring segment 11 contains the following means which are adapted to be used for positioning the cuvette ring segment in the analytical system:

a lip 16 which is integrated with the inner side walls 42 and extends radially from the latter on the outside of the chambers, the bottom wall 36 of at least one of the chambers, for example the chamber 12-4, has a projection 14 which extends from the outside of the bottom wall along the longitudinal axis of the chamber.

The shaping of the lip 16, shown in the attached figures, and a corresponding guide or lock in the cuvette carrier (not shown in the attached figures) of the analysis system ensure that, when the cuvette arrangement according to the invention is inserted into th analysis system, the windows of all the chambers are located in the correct position, and in particular at the correct height, which is necessary for carrying out optical measurements with the optical measuring instruments provided in the analysis system. During such a measurement, a light beam traverses, for example, the window parts 45, 46 of the chamber 12-4 along the axis Y—Y, as shown in FIG. 4.

The projection 14 in the form of a truncated cone and a corresponding guide in the cuvette carrier of the analysis system ensure that, when the cuvette ring segment 11 is used in the analysis system, the longitudinal axis Z—Z of each chamber is perpendicular to the light beam along the axis Y—Y. In this way, the projection 14 also provides for an even more accurate positioning of the cuvette ring segment in the analysis system.

Since the cuvette ring segment in FIG. 1 is relatively long, two projections 14, 15 are provided therein at the chambers 12-4 and 12-9 respectively. With shorter cuvette ring segments, however, a single projection, for example the projection 14, suffices for accurate positioning of the cuvette ring segment. The projections 14 and 15 are preferably hollow.

In addition, the cuvette ring segment 11 contains a lip 17 which is integrated with the outer side walls 41 and extends radially outwards. This lip facilitates handling of the cuvette ring segment by the user, in particular when the segment has to be taken out of the analysis system.

What is claimed is:

1. A cuvette arrangement for use in a chemical analysis system, which cuvette arrangement comprises an integrally formed, partially annular unit which defines a plurality of chambers for the receipt of sample-reagent mixtures, wherein each chamber includes the following elements:

(a) an open and a closed end,
  (b) an outer side wall forming an outer edge which fits into a first arc,
  (c) an inner side wall forming an inner edge which fits into a second arc concentric with the first arc,
  (d) a bottom wall extending between the outer and inner side walls at the closed end of the chamber, and
  (e) windows which enable radiation energy to be transmitted through the chamber with low loss and free from distortion, which windows comprise a pair of flat, mutually parallel parts which are separated from one another by a defined distance, one of the flat parts in each pair being integrated with the outer side wall and the other of the flat parts in each pair being integrated with the inner side wall, said annular unit also including means for positioning it in the chemical analysis system, which positioning means comprises the following elements:

(f) a lip which is integrated with the inner side walls and extends radially from the latter on the outside of the chambers, and
  (g) a projection which extends from the outside of the bottom wall of at least one of the chambers and along the longitudinal axis of the chamber.

2. A cuvette arrangement according to claim 1, which contains a plurality of partitions integrated with the outer side walls, the inner side walls and the bottom walls of the chambers, each partition having an upper section which is substantially parallel to the longitudinal axis of each chamber and one end of which is adjacent to the open end of the cuvette arrangement, a first lower section integrated with the bottom wall of a first chamber, and a second lower section integrated with the bottom wall of a second chamber, the first and second lower sections being separated by an air space.

* * * * *